United States Patent [19]

Gysin et al.

[11] Patent Number: 5,192,807
[45] Date of Patent: Mar. 9, 1993

[54] SIDEROPHORES AS ANTIPARASITIC AGENTS

[75] Inventors: Jurg Gysin; Yves Crenn, both of Cayenne; Luiz Pereira da Silva; Catherine Breton, both of Paris, all of France

[73] Assignee: Institut Pasteur, Paris Cedex, France

[21] Appl. No.: 762,086

[22] Filed: Sep. 19, 1991

Related U.S. Application Data

[63] Continuation of Ser. No. 372,370, Jul. 21, 1989, abandoned.

[30] Foreign Application Priority Data

Oct. 2, 1987 [FR] France ................. 87 13623

[51] Int. Cl.$^5$ ............................................. A01N 37/18
[52] U.S. Cl. ..................... 514/563; 435/280; 435/803; 435/852; 562/564
[58] Field of Search ............. 562/564; 514/563; 435/106, 280, 803, 852

[56] References Cited

U.S. PATENT DOCUMENTS 4,600,691 7/1986 Chaiet et al. ................... 435/106

OTHER PUBLICATIONS

Pierre et al. Ann. Pharma. Francaises, 44, p. 255, 1986.
Favier et al. Ann. Pharma. Francaises, 44, p. 329, 1986.
Nassif et al. Infec. & Immunity, 54, p. 603, 1986.
Scheibel et al. Mol. Pharmacol. 30, p. 364 (1986).
J. Clin. Microbiol., vol. 25, pp. 378–379 (1987).
Journal of Medicinal Chemistry, vol. 15, No. 11, 1972, J. B. Hynes et al.: "Hydroxylamine derivatives as potential antimalarial agents. 2. Hydroxamates and amidoximes", pp. 1194–1195.

Primary Examiner—Thurman K. Page
Assistant Examiner—G. S. Kishore
Attorney, Agent, or Firm—Oblon, Spivak, McClelland, Maier & Neustadt

[57] ABSTRACT

Antiparasitic agents constituted by a siderophore substance including at least one hydroxamate group, at least one peptide bond, and having a molecular weight of less than 1,000 D, e.g. aerobactin. A method of isolating antiparasitic agents by purification from the supernatant of a culture of an appropriate bacteria such as pathogenic enterobacteria applicable as antiparasitic agents, in particular as antimalarial agents.

3 Claims, 6 Drawing Sheets

SIDEROPHORES AS ANTIPARASITIC AGENTS

This application is a continuation of application Ser. No. 07/372,370, filed on Jul. 21, 1989, now abandoned.

The present invention relates to endogenous parasite inhibiting bacterial siderophore products, to methods of obtaining such products, and to antiparasitic compositions and in particular antimalaria compositions containing said products.

In the literature, it is specified that iron is an essential element for microbe development. However, although iron in the ferric form is widely distributed in nature, it has very low solubility and therefore it is directly available to a small extent only without the aid of mechanisms having a high affinity for such ferric forms and suitable for passing them through the bacterial wall, thereby enabling bacteria to multiply, in particular when the medium is iron-poor.

Enterobacteriaceae secrete enterochelin which is an iron chelator having a phenolic structure; and some strains of *Escherichia coli*, *Aerobacter aerogenes*, *Salmonella sp.*, and *Klebsiella pneumoniae*, interalia, also secrete a non-phenolic iron chelator called aerobactin.

In an article by Warner et al, (Inf. Immun. 1981, 33, 2, pp. 540–545) it is specified that *E. coli* synthesizes aerobactin whose genetic determinants are situated on plasmids called ColV plasmid since they are identified as being capable of promoting synthesis of Colicin V.

The Inventors have also observed that *Klebsiella pneumoniae* provides partial protection to sagouin marmosets against infection by *Plasmodium falciparum*.

It is shown in an article by Nassif (Inf. Immun. 1986, 54, 3, pp. 603–608) that one of the virulence factors in some strains of *Klebsiella pneumoniae* is the production of aerobactin by said strains.

In addition, only those strains which are capable of producing aerobactin can continue to multiply in an iron-poor medium.

The production of aerobactin is related to the presence of a plasmid.

It is specified in an article by Williams et al, (Inf. Immun. 1986, 51, 3, pp. 942–947) that although aerobactin has a lower affinity for ferric derivatives than enterochelin, it possesses regulation and physiological properties which enable larger quantities of iron to be provided for bacteria growth than can be provided by enterochelin. Aerobactin stimulates bacterial growth at concentrations which are 500 times smaller than enterochelin.

In addition, Clark et al have shown (Nature, 1976, 259, 309–311, and Parasitol., 1977, 74, 9–18) that some species of bacteria are recognized as having immunostimulating properties and are used to protect mice against the murine parasite *Babesia spp.* and against *Plasmodium spp.*

Some compounds exhibiting action against parasites are described in the prior art.

In particular:

Quinine which acts by fixing on the DNA of schizonts, essentially on young forms, and which destroys them in two to four days; however it has a degree of toxicity.

Derivatives of 4-aminoquinoline, in particular chloroquine, which act by inhibiting parasite DNA polymerase, preventing replication and destroying the parasites in two to four days. These derivatives do not present significant toxicity, however more and more strains, in particular of *Plasmodium falciparum* are resistant to these derivatives.

The object of the present invention is to provide a new family of antiparasitic agents having specific action against endocellular parasites, in particular those contained in human red blood cells, which differ from prior art antiparasitic agents in that they act by means of a mechanism which is totally different and original in this field, namely an iron chelator action, which starves the parasite of iron, and which is associated with the action of a toxin, thereby providing treatments which are effective more quickly and at lower doses than when using prior art compounds, and in addition anti-parasitic agents of the invention have a lower degree of toxicity.

The present invention provides an antiparasitic agent characterized in that it is constituted by a siderophore substance including at least one hydroxamate group, at least one peptide bond, and a molecular weight of less than 1,000 D, in that it exhibits the property of penetrating into cells, in particular into red blood cells in order to exert its antiparasitic activity, in particular against malaria, which activity is specific to endocellular parasites, in particular those contained in red blood cells, and is not reversed by iron, said activity being referred to by the term "plasmocidin" activity.

In an advantageous embodiment of the antiparasitic agent of the present invention, it is characterized in that it satisfies formula I below:

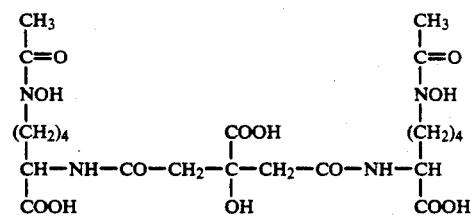

which formula also encompasses substances derived therefrom by substitution, and in that it exhibits plasmocidin activity.

Substances satisfying formula I inhibit the multiplication of endocellular parasites by a combined action of an iron chelator and of a toxin.

Said compounds of the invention are non-toxic both for man and for animals.

The present invention also provides a method of obtaining the antiparasitic agent of the invention by bacterial synthesis, said method being characterized in that the bacteria used is a pathogenous enterobacteria and in that the resulting agent is purified from the supernatant of the culture of said bacteria, as cultivated in a medium having no iron.

In an advantageous implementation of the method, said bacteria is K5a 1101 *Klebsiella pneumoniae*.

In a preferred disposition of this implementation, the supernatant of the culture containing said agent introduced in an iron exchange chromatographic column and is then eluted.

In an advantageous implementation of this disposition, the portion of the eluate containing said substances is subjected to filtering on Sephadex G50 gel.

The active components of the invention may be formulated in antiparasitic compositions.

According to another aspect of the present invention, pharmaceutical compositions are provided containing an effective amount of at least one antiparasitic agent of the invention, exhibiting plasmocidin activity both in man and in animals, optionally associated with an appropriate vehicle for administration.

The pharmaceutical compositions may be administered, in particular, orally or parenterally. When administered orally, said compositions may be presented in slow release form, in particular by the active ingredients being adsorbed on calcium phosphate.

In addition to the above dispositions, the invention also includes other dispositions which appear from the following description.

The invention will be better understood from the additional description below which refers to examples of preparing substances in accordance with the invention and of demonstrating the antiparasitic activity of said substances of the invention.

However, it should naturally be understood that these examples are given purely to illustrate the invention and that they do not constitute a limitation thereon.

EXAMPLE

EXAMPLE 1

Figure 1:
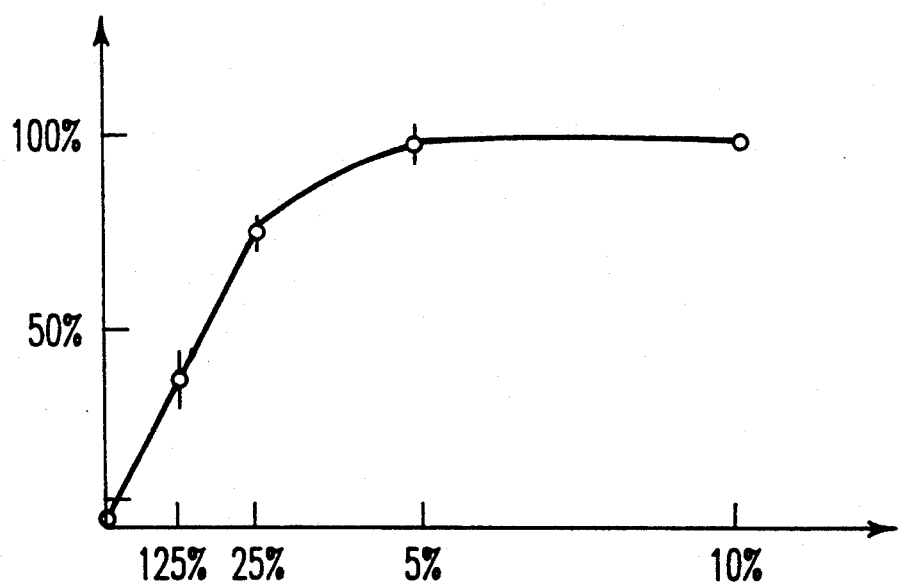
FIG. 1 is a plot of the concentration of aerobactin and the percentage of Schizonts killed.

Tests for characterizing the antiparasitic activity of substances in accordance with the present invention, referred to as "plasmocidin" activity 1. Demonstrating the inhibition of parasite multiplication In vitro, this inhibition is associated with secretion by bacteria of a hydroxamate substance which chelates iron, which has a MW=300, and which is called aerobactin. Plasmocidin activity was observed as a function of the bacteria culture medium (Table I) and of the final concentration (expressed in %) of aerobactrin, calculated on the basis of a hydroxamate titration of the bacteria supernatant in the parasite culture medium (Table II). The culture supernatant of *Klebsiella pneumoniae* K5a was applied to cultures of *Plasmodium falciparum* as described in Table I. The percentage of schizonts killed was estimated as indicated in FIG. 1. This inhibition could be observed only when the bacteria were placed in iron-free culture mediums such as M9 or RPMI.

Table I shows the plasmocidin activity of aerobactin as a function of the culture medium (iron-free or otherwise).

TABLE I

| Culture Medium | Bacterial Growth | Rate of Increase of the Parasitemia | |
|---|---|---|---|
| | | Day 1 | Day 3 |
| L broth[1] | — | 3 to 5 | 10 to 20 |
| | + | 3 to 5 | 10 to 20 |
| RPMI[2] | — | 3 to 5 | 10 to 20 |
| | + | 1 | 1 |
| RPMI*[3] | — | 3 to 5 | 10 to 20 |
| | + | 0.02 | 0.02 |
| RPMI* + Fe | — | 3 to 5 | 10 to 20 |
| | + | 3 to 5 | 10 to 20 |
| M9[4] | — | 3 to 5 | 10 to 20 |
| | + | 0.01 | 0.02 |
| M9 + Fe | — | 3 to 5 | 10 to 20 |
| | + | 3 to 5 | 10 to 20 |

[1] and [4] are described by Nassif et al (Infect. Immun., 1986, 54, 603-608).
[2] is liquid (GIBCO) and is supplemented with glutamine.
[3] is an RPMI medium modified to allow *P. falciparum* to grow without addition of human serum.

*Klebsiella pneumoniae* K5a 1101 is cultured in various media as indicated in the above table and harvested at $A_{526}$ nm = 1.

The culture supernatant is filtered (using 0.22 μm Millex filters) and introduced in the culture medium of a strain of *Plasmodium falciparum* FUP, the parasites being cultivated as described by Trager et al (Science, 1976, 193, pp. 673-675) and synchronized using the technique developed by Lambros et al (J. Parasitol., 1979, 65, pp. 418-420).

The initial parasitemia was at 1% to 2% and the parasites were at the beginning of the schizont phase. "+" supernatant was taken from the culture of *Klebsiella pneumoniae*; "—" supernatant was a control supernatant (without bacterial growth).

The supernatant was introduced into the medium to a final concentration of 10% aerobactin, with the concentration being calculated from hydroxamate titration. The parasitemia was monitored for three days after addition of supernatant and estimated by counting at least 5,000 red blood cells on Giemsa stained smears.

"+Fe" means that 100 μm of $FeCl_3$ were added to the parasite culture at the same time as the supernatant.

The results are averages of three independent experiments.

Table II specifies the plasmocidin activity of aerobactin as a function of its final concentration calculated on the basis of the hydroxamate titration of the culture supernatant.

TABLE II

| Supernatant | Final Concentration | Rate of Increase of Parasitemia | | |
|---|---|---|---|---|
| | | Day 1 (rings) | Day 2 (schizonts) | Day 3 (rings) |
| K. pneumoniae /RPMI* | 10% | 0.02 | 0.02 | 0.02 |
| | 5% | 0.1 | 0.1 | 0.02 |
| | 2.5% | 1 | 1 | 1 |
| | 1.25% | 2 to 3 | 2 to 3 | 5 to 8 |
| RPMI* | 1.25%–10% | 3 to 5 | 3 to 5 | 10 to 20 |

The experiments were performed under the same conditions as those described for Table I.

The culture supernatant of *Klebsiella pneumoniae* K5a 1101 developed in an RPMI medium was introduced at different concentrations in aerobactin (calculated on the basis of hydroxamate titration) into cultures of *Plasmodium falciparum*. The results are taken from two independent experiments.

The results given in Table II make it possible to plot the dose/response curve shown in FIG. 1. The final concentration of aerobactin is plotted along the X axis, and calculated from hydroxamate titration of the supernatant of *K. pneumaniae* culture, and expressed in percentage, and the percentage of schizonts killed is plotted up the Y axis.

This curve shows the plasmocidin activity of aerobactin.

The activity of the supernatant was evaluated by calculating the rate of increase of the parasitemia during each parasite cycle.

This curve agrees with the effects observed after an intravenous injection of a supernatant of *Klebsiella pneumoniae* culture given to monkeys infected with *Plasmodium falciparum*.

In vitro, the supernatant of *Klebsiella pneumoniae* K5a culture thus inhibits *Plasmodium falciparum* from multiplying in culture in human red blood cells.

The schizonts are observed to degenerate.

In vivo, Saimiri sciureus monkeys infected with *Klebsiella pneumoniae* K5a show a degree of resistance to infection by *Plasmodium falciparum*. This "resistance" has been associated with secretion by the bacteria of one or more substances having a molecular weight of 1,000. If monkeys parasitized by *Plasmodium falciparum* receive a peritoneal injection of supernatant of K5a strain culture that has been filtered and depleted of substances having a MW > 1,000, it is observed that parasite multiplication is inhibited (FIG. 2).

Figure 2:
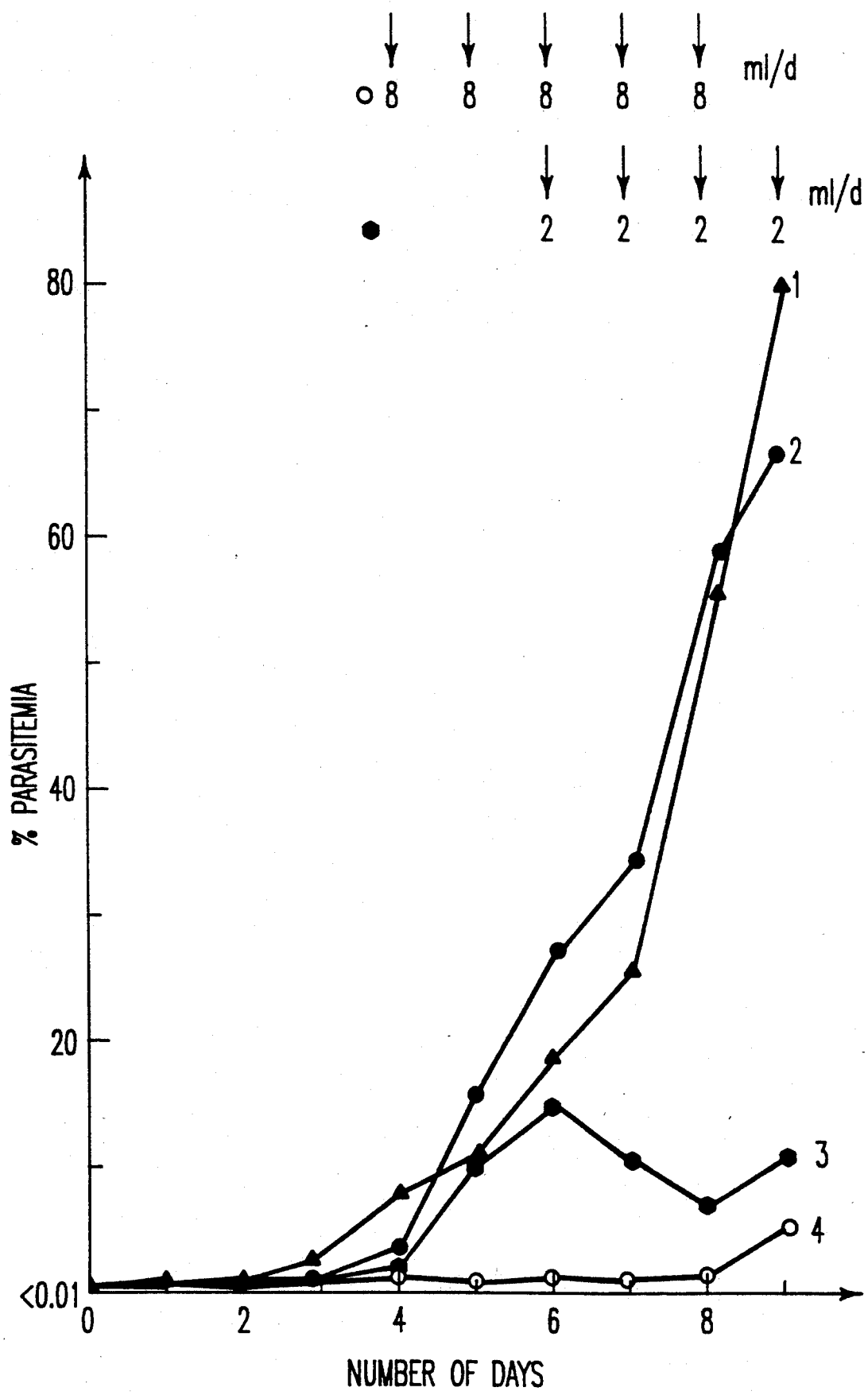
FIG. 2 is a plot of infection in days and the degree of para sitemia.

FIG. 2 has the duration of infection in days plotted along the X axis and the degree of parasitemia expressed in percentage plotted along the Y axis.

Four monkeys were infected with $10^8$ parasites (day 0).

The aerobactin is partially purified from a supernatant of K5a *Klebsiella pneumoniae* culture by successive filtrations through AMICON PM30, AMICON PM10, and UM2 membranes.

The fraction that is not retained by the membranes, and which therefore has a molecular weight of less than 1,000, was used.

Monkeys Nos. 1 and 2 were controls.

Monkeys Nos. 3 and 4 were infected as described above.

Peritoneal injections of aerobactin began on day four (D=4).

The doses injected are expressed in milliliters per day (ml/d) and are given in Table III below.

TABLE III

| MONKEY | DOSES (in ml/d) D4 | D5 | D6 | D7 | D8 | D9 |
|---|---|---|---|---|---|---|
| Monkey No. 3 | — | — | 2 | 2 | 2 | 2 |

TABLE III-continued

| MONKEY | DOSES (in ml/d) D4 | D5 | D6 | D7 | D8 | D9 |
|---|---|---|---|---|---|---|
| Monkey No. 4 | 8 | 8 | 8 | 8 | 8 | — |

Parasitemia was measured each day, two hours before the injection, by counting at least 5,000 red blood cells on blood Giemsa stained smears.

2. Identification of the Plasmocidin agent

The plasmocidin activity was studied on the basis of strains of *Klebsiella pneumoniae* of differing serotype or virulence (Table IV).

TABLE IV

| Strain of Bacteria | Serotype | Virulence | Growth Medium | Final Concentration | % Schizonts Killed | $A_{526\ nm}$ |
|---|---|---|---|---|---|---|
| 1101 | K5 | + | RPMI* | 20% | 99% | |
| and | | | | 10% | 99% | 0.15 |
| 1102 | | | | 5% | 95% to 98% | to |
| | | | | 2.5% | 60% to 70% | 0.20 |
| | | | RPMI* + Fe | 2.5% to 20% | 0 | 0.01 |
| 7825 | K1 | + | RPMI* | 20% | 95% to 99% | |
| | | | | 10% | 65% to 75% | 0.10 |
| | | | | 5% | 50% to 60% | to |
| | | | | 2.5% | 30% to 40% | 0.15 |
| | | | RPMI* + Fe | 2.5% to 20% | 0 | 0.005 |
| 52144 | K1 | − | RPMI* | 2.5% to 20% | 0 | 0.005 |
| | | | RPMI* + Fe | 2.5% to 20% | 0 | 0.005 |

K5a strains 1101 and 1102 were isolated from infected Saimiri sciureus monkeys. *K. pneumoniae* 7825 and 52144 are described in Nassif (Inf. Immun., 1986, 54, 3, pp. 603–608). The nomenclature used for the serotypes corresponds to that of C. Richard [Bull. Inst. Pasteur (Paris), 1982, 80, pp. 127–145].

The virulent K5a 1101 and K1 7825 strains exhibit plasmocidin activity whereas the non-virulent K1 52144 strain does not exhibit such activity.

It has been shown that the non-virulence of the K1 52144 strain is related to its non-production of aerobactin (X. Nassif, P. J. Sansonetti, Infect. Immunol., 1986, 54, pp. 603–608).

The production of hydroxamate was measured on a 200 μl sample of supernatants, as described in Csaky (Acta. Chem. Scan., 1948, 2, pp. 450–454).

Toxicity with respect to *Plasmodium falciparum* is associated with a purification peak for aerobactin obtained by ion exchange column (Dowex) and filtering on Sephadex G50 gel (see FIG. 3).

FIG. 3 shows that the plasmocidin activity subsists after the aerobactin has been purified.

The results suggest that the plasmocidin activity is a property of aerobactin.

Aerobactin was purified from a supernatant of K5a 1101 *Klebsiella pneumoniae* culture cultivated in an RPMI* medium.

FIG. 3*a*: a culture supernatant (500 ml at a pH 7.0) was placed in a Dowex-1 column (25×2 cm) and eluted with 500 ml of an ammonia chloride gradient running from 0.4M to 1.0M at a flow rate of 30 ml/h. 2.5 ml fractions were collected and the hydroxamate was measured using the Csaky method.

FIG. 3*b*: the pool of hydroxamate (10 ml to 15 ml) collected by the ion exchange chromatography was placed in a Sephadex G50 column (25×2 cm) and eluted with 100 mM of phosphate buffer (pH 7.0), at a flow rate of 30 ml/h. Fractions (2 ml to 3 ml) were collected and the hydroxamate measured ($A_{526\ nm}$ absorbance—●—), and the following were also measured: inhibition of Plasmodium falciparum growth (—○—) and A220 nm absorbance (—△—).

Inhibition of Plasmodium falciparum growth:

0.2 μm of the filtered fractions were placed in a synchronized culture of Plasmodium falciparum at a final concentration of 2.5%, as described in Table I. 100 μCi/ml of methionine marked with sulfur 35 (Amersham) were added on day 1 (rings). The parasite culture was collected on day 2 (schizonts) and the incorporation of $^{35}$S-methionine was measured in 10% TCA.

The concentration of aerobactin in the hydroxamate pool collected after filtering on a gel was estimated by comparison with the hydroxamate content of a solution of L-Lysine hydroxamate at a known concentration.

3. Demonstration of antiparasitic action

The antiplasmodial action of three iron chelators was compared in vitro with respect to Plasmodium falciparum, and the effect of adding iron to the parasite culture was also studied (FIG. 4).

L-Lysine hydroxamate hydrochloride does not exhibit antiplasmodial activity, thereby indicating that the hydroxamate group does not intervene alone in the plasmocidal activity of aerobactin.

Desferioxamine, an iron chelating hydroxamate used for causing iron deprivation in man when overloaded with iron inhibits parasite growth.

The inhibition of desferioxamine is totally reversed by adding iron to the parasite culture.

In contrast, adding iron to parasite cultures treated with aerobactin does not reverse the plasmocidin action of the aerobactin.

Thus, iron deprivation plays a part in the antiplasmodial activity of desferioxamine but not in the plasmocidin activity of aerobactin. This indicates that aerobactin probably acts as a toxin and not merely by iron deprivation.

Figure 3A:
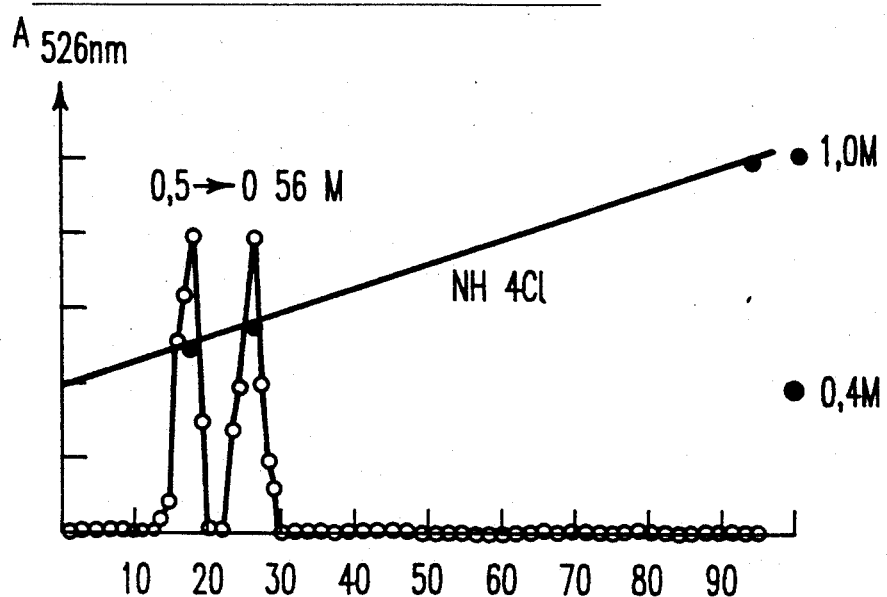
FIG. 3a shows elution profile of aerobactin on DOWEX-1 column.
Figure 3B:
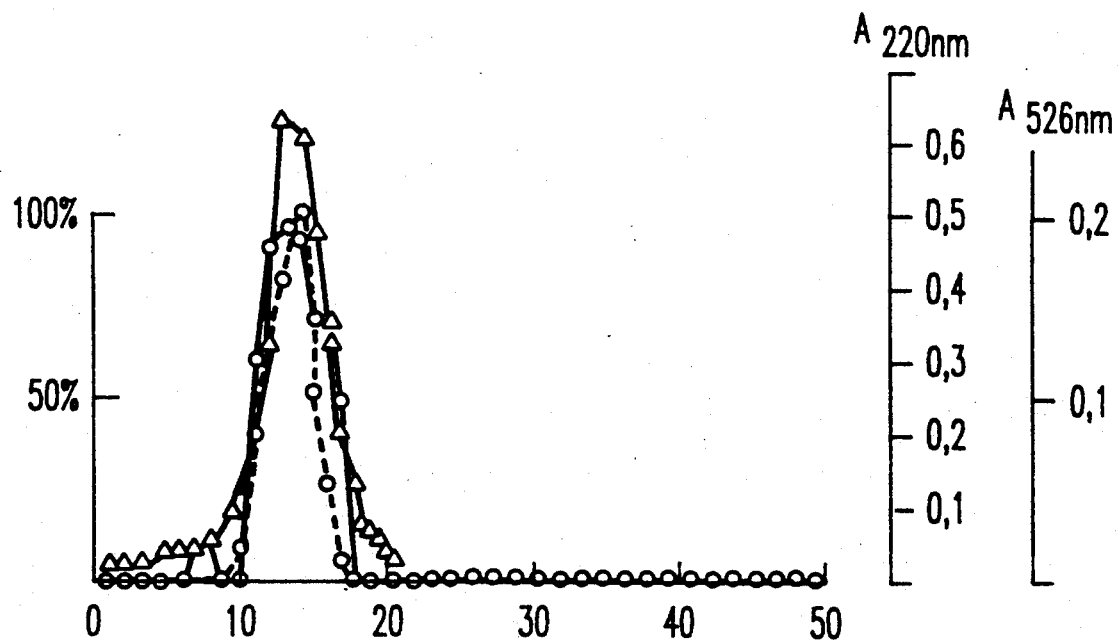
FIG. 3b shows the Sephadex G50 elution pattern.
Figure 4A:
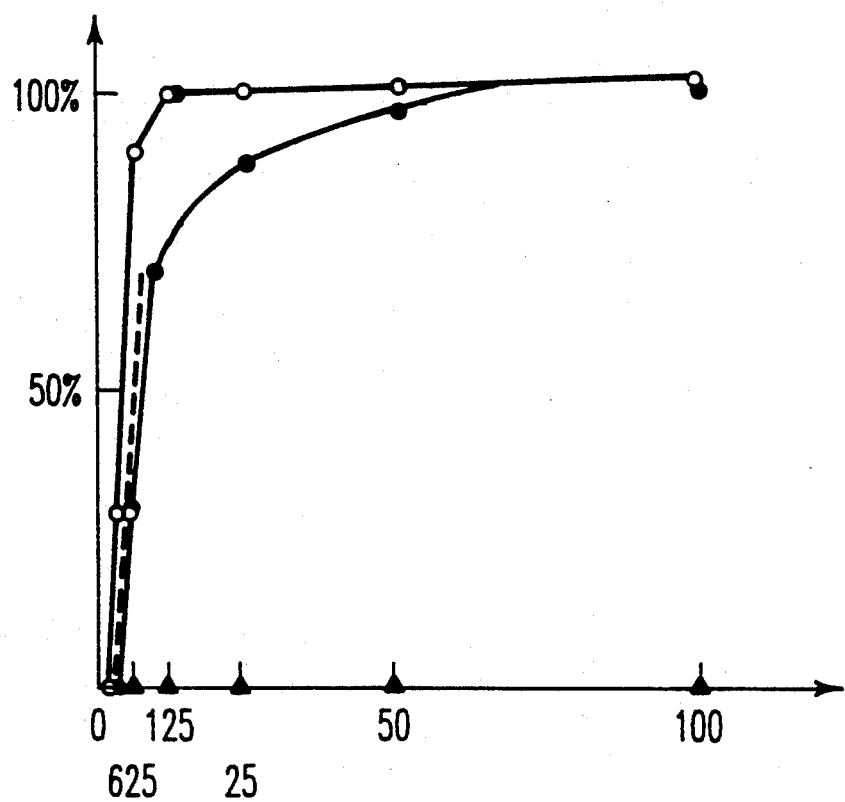
FIG. 4a shows the inhbition of growth of plasmidium falciparum by L-Lysine hydroxamate (—▲—), by desferioxamaine (—●—) and aerobactin (—○—).

FIG. 4a shows how the growth of Plasmodium falciparum is inhibited by L-Lysine hydroxamate (—▲—), by desferioxamaine (—●—), and by aerobactin (—○—), with measurements being performed as described with respect to FIG. 3.

Adding $2.10^{-3}$M of $FeCl_3$ to the parasite culture immediately after the hydroxamate has little effect on inhibition due to aerobactin (—○—), whereas it completely reverses the inhibition due to desferioxamine (—▲—).

Figure 4B:
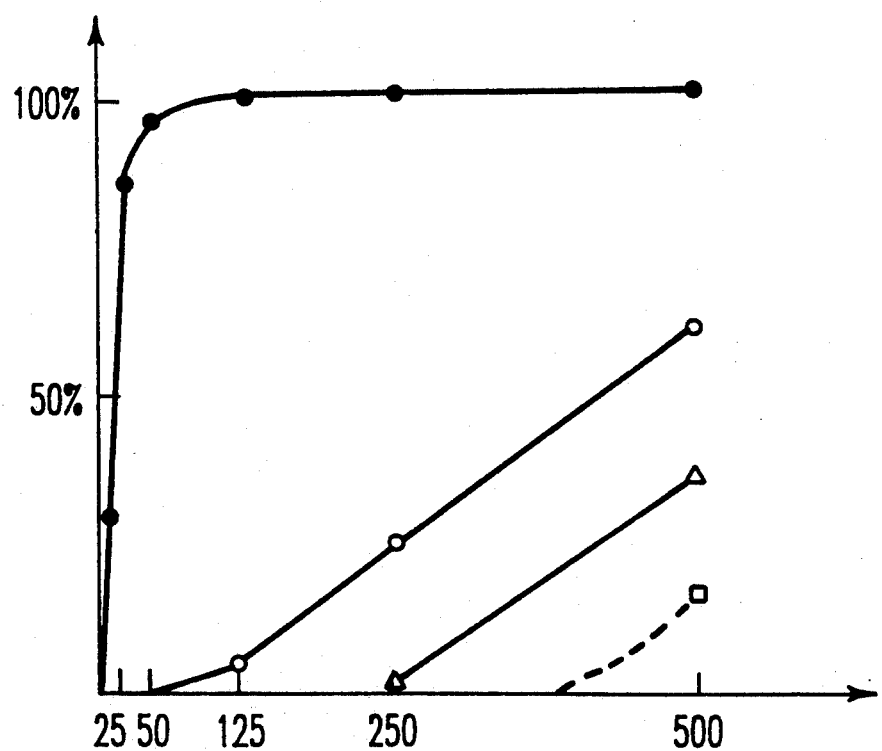
FIG. 4b shows the effect of the concentration of $FeCl_3$ on the inhibition by desferioxamine.

FIG. 4b shows the role played by the concentration of $FeCl_3$ in reversing the inhibition due to desferioxamine.

—●—  no $FeCl_3$
—○—  $2.10^{-4}$ M $FeCl_3$
—△—  $10^{-3}$ M $FeCl_3$
—□—  $2.10^{-3}$ M $FeCl_3$

4. Quantitative tests

Tests in vitro have shown, in particular, that aerobactin is capable of inhibiting the growth of Plasmodium falciparum 100% when at a concentration of 2.5 μg/ml (about $10^{-5}$M).

Figure 5:
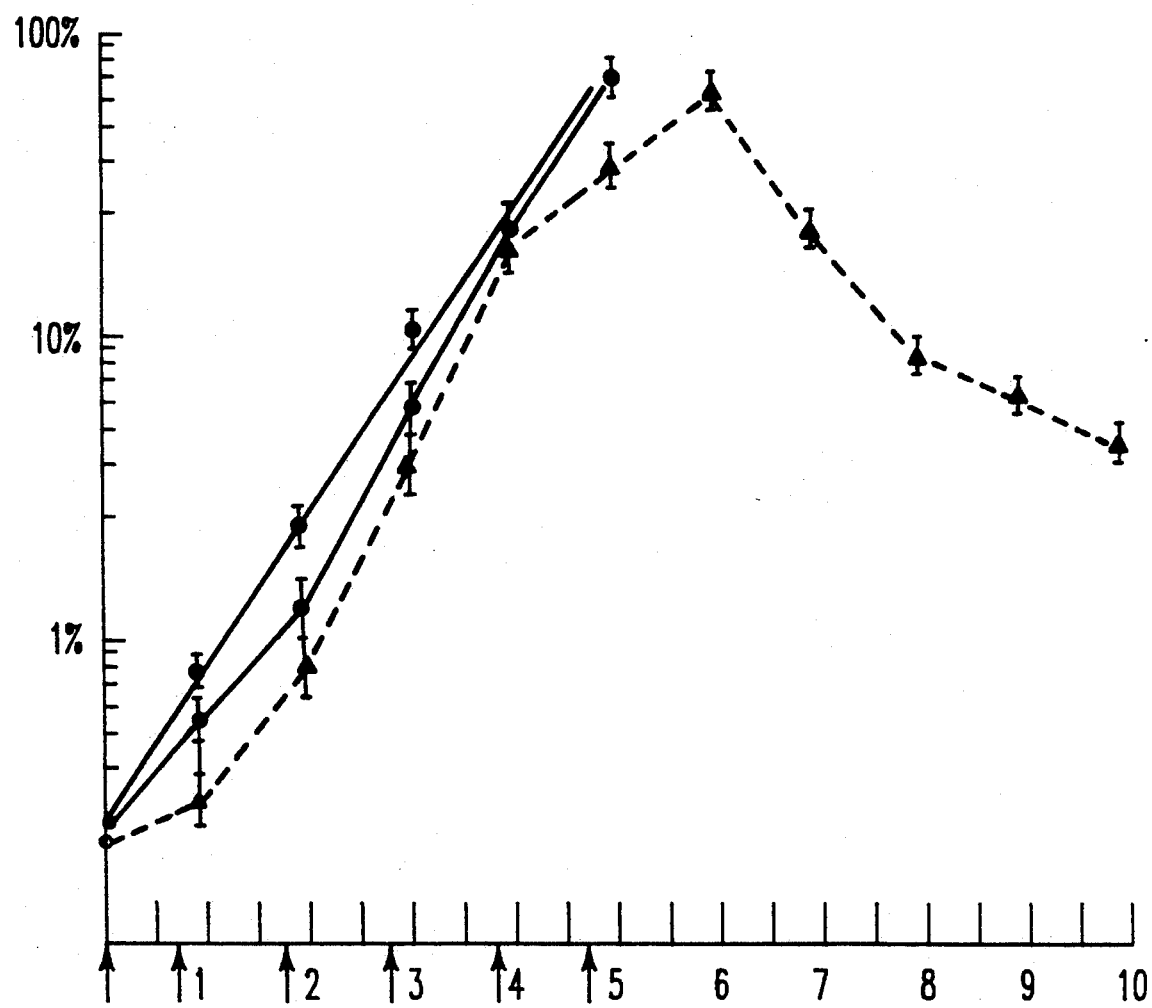
FIG. 5 is a plot of survival in days and the percentages by which parasite multiplication is slowed down.

Another test performed in vivo has shown that an intravenous injection (15 μg/mouse) of purified aerobactin given to mice infected with Plasmodium chaubaudi causes parasite multiplication to be slowed down, allowing the mice to survive, whereas mice treated with 7.5 μg of aerobactin or not treated at all do not survive, and given that an injection of aerobactin is not toxic for mice. The same effect has been observed for mice infected with P. falciparum as shown in FIG. 5, in which survival in days is plotted along the X axis and the percentage by which parasite multiplication is slowed down is plotted along the Y axis.

5. Specificity of the antiparasitic action

Another test has shown the specific action of aerobactin on parasitized cells. Aerobactin penetrates quickly into parasitized red blood cells and is concentrated by at least 200 times in the parasitized cell. It is not concentrated in healthy red blood cells. Desferioxamine does not penetrate into parasitized red blood cells.

This test studies the incorporation of tritium-marked lysine in normal red blood cells and in red blood cells infected with Plasmodium falciparum.

Figure 6:
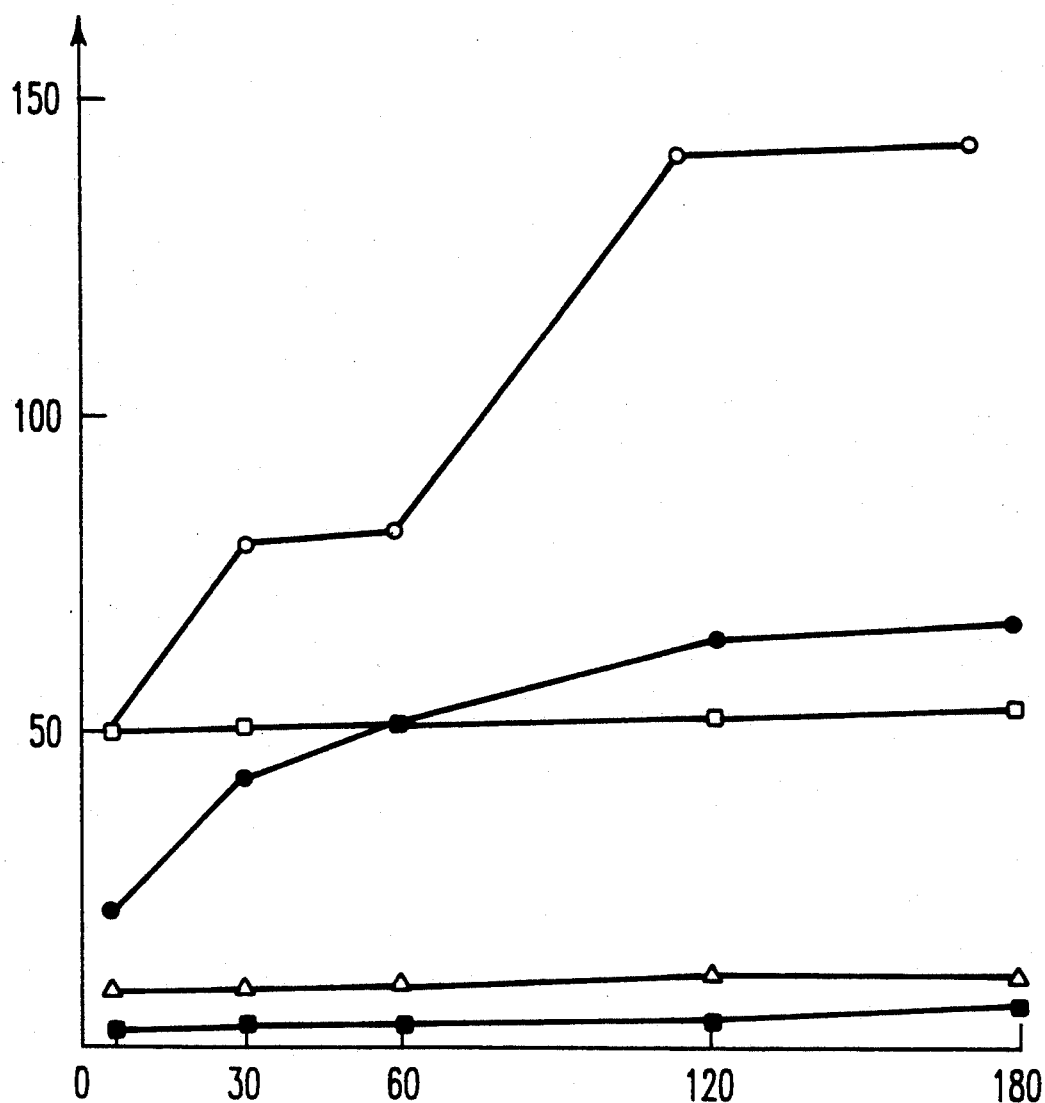
FIG. 6 is a plot of the incorporation of tritium-marked lysine in normal red blood cells and in reb blood cells infected with plasmodium falciparum.

FIG. 6 shows the results.

Tritium-marked aerobactin (0.2 mCi/mmol to 0.3 mCi/mmol) was purified as described above (FIG. 3) from a supernatant of strains of K5 1101 Klebsiella pneumoniae culture cultivated in an RPMI* medium containing 100 μCi/ml of tritium-marked lysine.

Desferioxamine marked with iodine 125 (50 mCi/mmol) was obtained by the iodine-producing technique.

The tritium-containing aerobactin (7 μg/ml) and the $^{125}$I containing desferioxamine (50 μg/ml) were introduced into synchronized cultures of Plasmodium falciparum (schizont stage, 20% parasitemia, hematocrit: 5%) and in a suspension of red blood cells (5% hematocrit). The cultures were incubated at 37° C. and 50 μl samples were taken at different times.

For each sample, the following were measured:
1. The cpm in the culture supernatant;
2. The cpm in the supernatant of red blood cells lysis (the red blood cells were lysed in 40 vol. of RPMI diluted ten times and the free parasites were precipitated using a centrifuge rotating at 5,000 rpm for 5 min and were washed in RPMI); and
3. The cpm associated with free parasites.

The parasites are subsequently lysed in order to prepare soluble and membrane fractions as described previously (Braun-Breton et al, Molecular Biochem. Parasitol., 1986, 20, pp. 33–43).

The radioactivity is essentially to be found in the soluble fraction since the intraparasitic aerobactin is recovered in the soluble fraction of the parasites.

Aerobactin is not detected in the cytoplasm of the red blood cells.

—△—: extracellular aerobactin
—●—: aerobactin associated with red blood cells
—○—: aerobactin associated with parasites
—□—: extracellular desferioxamine
—■—: intracellular desferioxamine 6. Study of the toxicity of substances in accordance with the invention Another test on the toxicity of substances in accordance with the invention shows that no toxic effect has been observed in mice or monkeys after aerobactin has been injected.

In addition, adding purified aerobactin to a culture of fibroblasts has no toxic effect on the cells.

7. Kinetics of the action on the parasites

Figure 7:
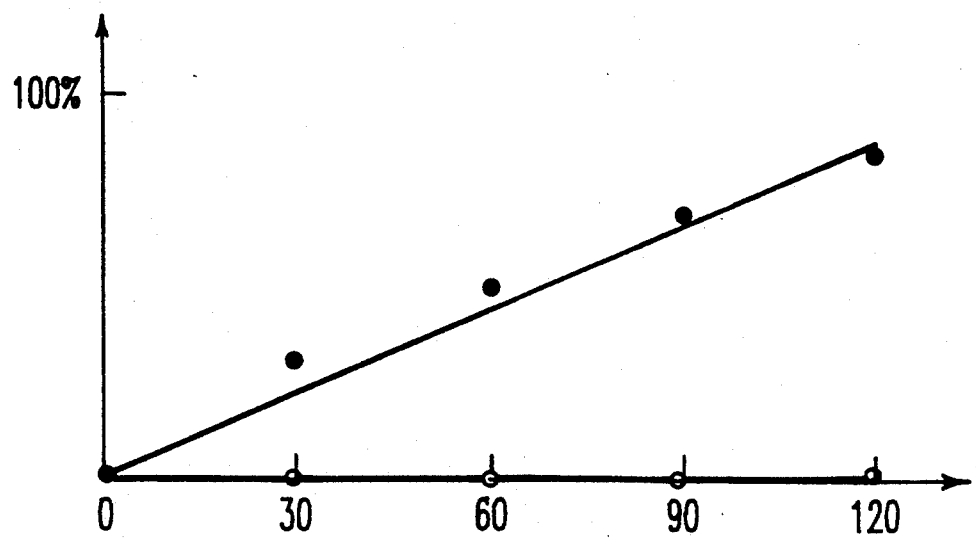
FIG. 7 is the kinetics of the action of aerobactin on the parasites.

As indicated in FIG. 7, aerobactin quickly suppresses the incorporation of $^{35}$S-methionine in the proteins of schizonts.

Time in minutes is plotted along the X axis and the percentage of inhibited schizonts is plotted up the Y axis.

The operating conditions were as follows:

The schizonts of *Plasmodium falciparum* were concentrated from a culture, they were washed and cultured at 37° C. for one hour. Solutions of hydroxamate (—●—50 μg/ml aerobactin and —○—500 μg/ml of desferioxamine) were added to the schizonts. Incubation at 37° C. continued and samples were taken at various different times. The hydroxamate was removed by washing the cells, and the cells were again cultured in the presence of 250 μCi/ml $^{35}$S-methionine for one hour.

The cultures were collected and the degree to which $^{35}$S-methionine had been incorporated was measured.

It can be seen that aerobactin inhibits the incorporation of methionine in 90% of schizonts within two hours, whereas desferioxamine has no action on the incorporation of methionine.

Such activity was not found when aerobactin was added to cultures of L fibroblasts for 5 hours.

We claim:

1. A method of killing *Plasmodium falciparum*, comprising administering to a man or an animal in need thereof an effective amount of an antiparasitic composition containing a siderophore substance with at least one hydroxamate group, which is able to penetrate red blood cells infected with *Plasmodium falciparum* and which is obtained by the method comprising:
   bacterial synthesis of said siderophore substance by a pathogenic enterobacteria *Klebsiella pneumoniae* of serotype K5 cultivated in an iron-depleted medium,
   isolating a siderophore substance excreted by said bacteria from the supernatant of the culture by introducing said supernatant in an anion exchange chromatographic column, followed by elution with a chloride gradient,
   collecting the fractions containing hydroxamate groups, and gel filtration of the pool of hydroxamate fractions collected by the ion exchange chromatography, followed by elution with an appropriate buffer.

2. A method according to claim 1, wherein said antiparasitic composition comprises a compound having the formula I below:

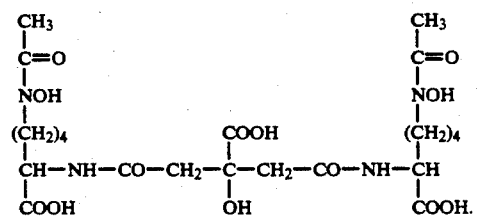

3. An antiparasitic composition having plasmocidin activity containing a siderophore substance with at least one hydroxamate group, which is able to penetrate red blood cells infected with *Plasmodium falciparum*, obtained by a method comprising:
   bacterial synthesis of said siderophore substance by a pathogenic enterobacteria cultivated in an iron-depleted medium;
   isolating said siderophore substance excreted by said bacteria from the supernatant of the culture by introducing said supernatant in an anion exchange chromatographic column, followed by elution with a chloride gradient;
   collecting the fractions containing hydroxamate groups; and gel filtration of the pool of hydroxamate collected by the anion exchange chromatography, followed by elution with an appropriate buffer, and
   wherein said pathogenic enterobacteria is Klebsiella of serotype K5.

* * * * *

UNITED STATES PATENT AND TRADEMARK OFFICE
CERTIFICATE OF CORRECTION

PATENT NO. : 5,192,807

DATED : March 9, 1993

INVENTOR(S) : Jurg Gysin et al.

It is certified that error appears in the above-identified patent and that said Letters Patent is hereby corrected as shown below:

On the title page, Item [30],

The Foreign Application Priority Data is incorrect, should read as follows: --Sep. 30, 1988 [PCT]   PCT.............PCT/FR88/00482

Oct. 2, 1987 [FR]  FRANCE..............87/13623--

Signed and Sealed this

Twenty-third Day of November, 1993

*Attest:*

BRUCE LEHMAN

*Attesting Officer*   *Commissioner of Patents and Trademarks*